US010709907B2

(12) United States Patent
Pan et al.

(10) Patent No.: US 10,709,907 B2
(45) Date of Patent: Jul. 14, 2020

(54) TAURINE AND ALOE SYNERGISTIC ANTI-IRRITANT COMPOSITIONS AND METHODS

(71) Applicant: Colgate-Palmolive Company, New York, NY (US)

(72) Inventors: Long Pan, Somerset, NJ (US); Jung Seo, Flanders, NJ (US); Zeenat Nabi, Cranbury, NJ (US); Shujiang Cheng, Warren, NJ (US); Nadia Soliman, East Brunswick, NJ (US); Laurence D. Du-Thumm, Princeton, NJ (US); Diana Scala, Hillsborough, NJ (US); Kyle Robbins, Toms River, NJ (US); Rahul Patel, Hillsborough, NJ (US); Marian Holerca, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/099,718

(22) PCT Filed: May 10, 2016

(86) PCT No.: PCT/US2016/031608
§ 371 (c)(1),
(2) Date: Nov. 8, 2018

(87) PCT Pub. No.: WO2017/196299
PCT Pub. Date: Nov. 16, 2017

(65) Prior Publication Data
US 2019/0183780 A1 Jun. 20, 2019

(51) Int. Cl.
| A61Q 15/00 | (2006.01) |
| A61K 8/97 | (2017.01) |
| A61K 8/46 | (2006.01) |
| A61K 8/26 | (2006.01) |
| A61K 8/28 | (2006.01) |
| A61K 8/9794 | (2017.01) |
| A61P 31/04 | (2006.01) |

(52) U.S. Cl.
CPC .............. *A61Q 15/00* (2013.01); *A61K 8/26* (2013.01); *A61K 8/28* (2013.01); *A61K 8/466* (2013.01); *A61K 8/97* (2013.01); *A61K 8/9794* (2017.08); *A61P 31/04* (2018.01); *A61K 2800/75* (2013.01)

(58) Field of Classification Search
None
See application file for complete search history.

(56) References Cited

U.S. PATENT DOCUMENTS

| 4,302,443 A | 11/1981 | Denavarre et al. |
| 4,593,046 A | 6/1986 | Gruber |
| 6,358,516 B1 * | 3/2002 | Harod .................. A61K 8/0208 424/401 |
| 8,647,681 B2 | 2/2014 | Markwell et al. |
| 2006/0008434 A1 * | 1/2006 | Knopf ...................... A61K 8/06 424/65 |
| 2016/0151265 A1 * | 6/2016 | Doering ................. A61K 8/365 424/68 |

FOREIGN PATENT DOCUMENTS

| CH | 0699182 | 1/2010 |
| DE | 102013216381 | 2/2015 |
| EP | 2263648 | 12/2010 |
| RU | 2456016 C2 | 1/2012 |
| WO | 1996/019183 | 6/1996 |
| WO | 2002/065997 | 8/2002 |
| WO | 2003/013439 | 2/2003 |
| WO | 2008/080764 | 7/2008 |
| WO | 2010/000877 | 1/2010 |
| WO | 2015/024567 | 2/2015 |

OTHER PUBLICATIONS

Jensen ("Targeting the IL-1 Family Members in Skin Inflammation", Curr Opin Investig Drugs. Nov. 2010; 11(11): p. 1211-1220) (Year: 2010).*
Corsini et al ("Endogenous Interleukin-1alpha Is Associated with Skin Irritation Induced by Tributyltin", Toxicology and Applied Pharmacology, vol. 138, p. 268-274 (1996)) (Year: 1996).*
Biotech Marine, 2015, "Hakkin-Gensui 500 Activating & Moisturizing Lotion," Mintel GNPD AN: 2907627.
Dr. Ci: Labo, 2011, "Gel," Mintel GNPD AN: 1650064.
Dr. Ci: Labo, 2012, "Gel," Mintel GNPD AN: 1967481.
Dr. Ci: Labo, 2013, "Aqua Collagen Gel Super Moisture EX," Mintel GNPD AN: 2016105.
Goldemberg, 1965, "Use of Anti-Irritants in Cosmetic Formulating," J. Soc. Cosmetic Chemists 16:317-340.
Goldemberg, 1977, "Reduction of topical irritation," J. Soc. Cosmet. Chem. 28:667-679.
Hoyu, 2015, "Base Up Bleach," Mintel GNPD AN: 3067573.
International Search Report and Written Opinion of the International Searching Authority in International Application No. PCT/US2016/031608, dated Jun. 27, 2016.
Japan Gateway, 2014, "Shampoo," Mintel GNPD AN: 2731321.
Korponyai et al., 2011, "Antiirritant properties of polyols and amino acids," Dermatitis, 22(3):141-146 PMID: 21569743.
Lindsey et al., 2002, "Cyclooxygenase inhibitory activity of Aloe species," South African Journal of Botany 68 (1):47-50.
Love Labo, 2012, "Shampoo," Mintel GNPD AN: 1905692.
Love Labo, 2012, "Treatment," Mintel GNPD AN: 1905723.
Misery et. al.; 2005, "[Sensitive skin in France: an epidemiological approach]," Ann. Dermatol. Venereol. 132 (5):425-429.
Mosmann, 1983, "Rapid colorimatric assay for cellular growth and survival. Application to proliferation and cytotoxicity assays," J. Immunological Methods 65:55-63.
Ozon, 2014, "Treament," Mintel GNPD AN: 2731319.
R&D Systems, 2019, Quantikine ELISA Human IL-1a/IL-1F1 Immunoassay Kit. R&D Systems, Minneapolis, MN.

(Continued)

*Primary Examiner* — Sin J Lee

(57) ABSTRACT

Personal care compositions containing active ingredients and an anti-irritant combination of aloe and taurine are disclosed. Methods of preparing the personal care composition and uses of the personal care composition are also disclosed.

17 Claims, 2 Drawing Sheets

(56) References Cited

OTHER PUBLICATIONS

Schwarzkopf & Henkel, 2008, "Calming Cream Conditioner," Mintel GNPD AN: 910145.
Schwarzkopf & Henkel, 2008, "Calming Cream Conditioner," Mintel GNPD AN: 911731.
Schwarzkopf & Henkel, 2008, "Calming Soothe Treatment," Mintel GNPD AN: 910164.
Schwarzkopf & Henkel, 2008, "Calming Soothe Treatment," Mintel GNPD AN: 915019.
Schwarzkopf & Henkel, 2008, "Calming Soothing Treatment," Mintel GNPD AN: 973626.
Schwarzkopf & Henkel, 2008, "Shampoo," Mintel GNPD AN: 910114.
Schwarzkopf & Henkel, 2008, "Shampoo," Mintel GNPD AN: 910497.
Schwarzkopf & Henkel, 2011, "Skin-Compatible Permanent Hair Colourant," Mintel GNPD AN: 1688927.
Schwarzkopf & Henkel, 2012, "Calming Cream Conditioner," Mintel GNPD AN: 1727312.
Schwarzkopf & Henkel, 2012, "Mild Conditioner," Mintel GNPD AN: 1768766.
Schwarzkopf & Henkel, 2012, "Mild Shampoo," Mintel GNPD AN: 1768984.
Schwarzkopf & Henkel, 2012, "Permanent Hair Colourant," Mintel GNPD AN: 1874641.
Schwarzkopf & Henkel, 2014, "Sensitive Soothe Shampoo," Mintel GNPD AN: 2635383.
Sexy U Products, 2010, "Energy Ultra Bronzing Tanning Lotion," Mintel GNPD AN: 1424603.
Watsons Personal Care Stores, 2011, "Facial Spray," Mintel GNPD AN: 1508050.
Anonymous, "Phenoxyethanol" [retrieved from internet-Wikipedia on Nov. 8, 2019].

\* cited by examiner

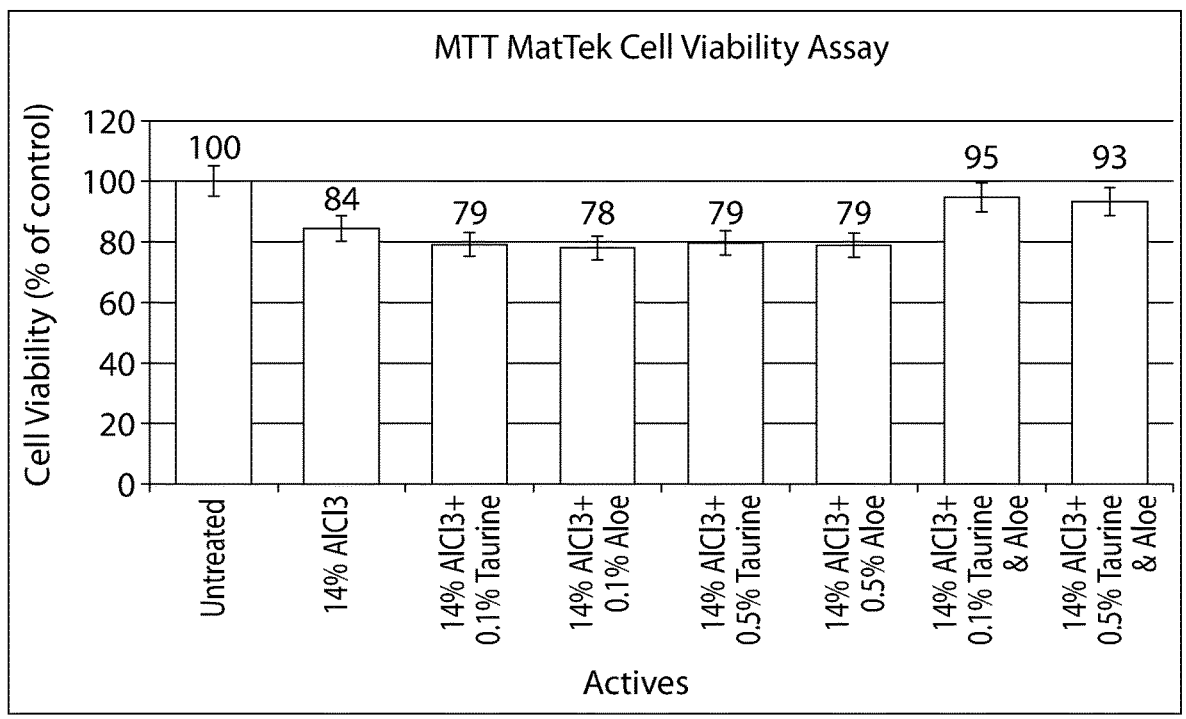
Figure 1: Mildness (MTT Assay) experiment results (MatTek 3D EpiDerm) reported as % cell viability

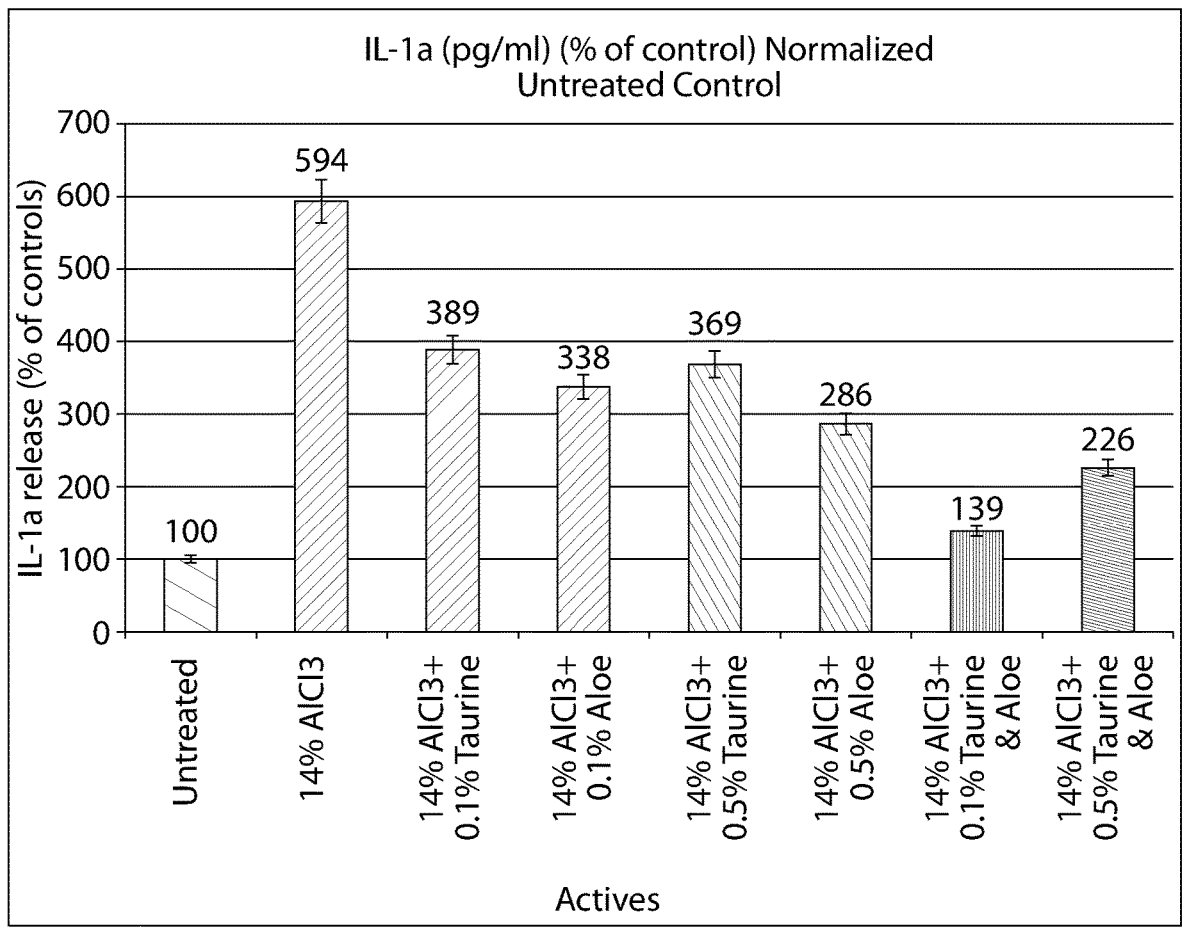
Figure 2: Irritation (IL-1α) experiment results
(MatTek 3D EpiDerm) reported in pg/mL (% of control)

TAURINE AND ALOE SYNERGISTIC ANTI-IRRITANT COMPOSITIONS AND METHODS

BACKGROUND

Antiperspirants based on aluminum or aluminum/zirconium salts are known. Underarm deodorants control odor by eliminating the bacteria that cause odor. Conventional antiperspirant salts tend to be acidic in aqueous solution, a property which makes them effective bactericides, thereby providing a deodorant benefit, but which can also cause skin irritation.

Long-acting antiperspirant compositions contain increased amounts of active ingredients as a route to obtaining sustained effectiveness. At the same time, skin sensitivity and vulnerability to various compounds may limit the practical upper concentration in personal care formulations. It is now believed that up to 50% of the population has sensitive skin with a reduced irritation threshold.

It is therefore desirable to develop and formulate efficacious anti-irritant ingredients into personal care products to mitigate potential irritant-induced redness, tingling, itching, or burning of the skin to a tolerable level for improved consumer compliance.

BRIEF SUMMARY

The present invention discloses that the use of taurine or aloe extract, individually, provides a beneficial reduction of the irritation caused by active ingredients commonly used in personal care products, such as antiperspirant compositions. However, more significantly, the present inventors have discovered that the combination of taurine and aloe extract provides a surprising synergistic reduction of the irritation which can be caused by active ingredients commonly used in personal care products, such as antiperspirant compositions.

In an embodiment, a personal care composition is provided for application to the skin or hair comprising a cosmetically acceptable carrier and an antiperspirant active ingredient in combination with aloe extract and taurine, wherein a total amount of aloe extract is 0.01 to about 5 weight percent, based on the total weight of the composition, and a total amount of taurine is 0.01 about 5 weight percent, based on the total weight of the composition.

In another embodiment, a method of forming a reduced irritation personal care composition is provided by mixing 10% to 30% antiperspirant active ingredient with 0.01 to 5 weight percent aloe extract and 0.01 to 5 weight percent taurine based on the total weight of the composition.

In further embodiment, the use of antiperspirant active and a combination of aloe extract and taurine to kill bacteria, reduce perspiration, and/or reduce body odor, wherein the aloe extract and taurine are present in a synergistic combination in which each is present in an amount from 0.01 to 1% by weight of the composition.

The invention also encompasses other personal care compositions for application to the skin, for example hand soaps or body washes, comprising a potentially irritating active ingredient and/or precursors thereof. The invention further provides methods of reducing sweat comprising applying the composition to skin, and methods of killing bacteria comprising contacting the bacteria with the composition.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a bar graph depicting the results of the MTT Assay experiment of Example 1, reported as % cell viability.

FIG. 2 is a bar graph depicting the results of the Irritation (IL-1α) experiment of Example 1, reported as a percentage of the test value for the Control, as measured in pg/mL.

DETAILED DESCRIPTION

The following description of the preferred embodiment(s) is merely exemplary in nature and is in no way intended to limit the invention, its application, or uses.

1. The invention therefore provides, in a first embodiment, a personal care composition for application to the skin or hair comprising a cosmetically acceptable carrier and about 2 to 40 weight percent of an active ingredient, in combination with aloe extract and taurine, wherein a total amount of aloe extract is 0.01 to 5 weight percent, and a total amount of taurine is 0.01 to 5 weight percent, all based on the total weight of the composition. (Composition 1), e.g., 1.1 Any of the foregoing compositions wherein the active ingredient is a metal-containing antiperspirant active ingredient.

1.2 Any of the foregoing compositions wherein the metal-containing antiperspirant active ingredient contains aluminum, zirconium, zinc or a combination thereof.

1.3 Any of the foregoing compositions wherein the metal-containing antiperspirant active ingredient is present in an amount of 5 to 40% by weight of the composition, optionally from 6, 7, 8, 9, 10, 11, 12, 13, or 14% up to 40% by weight of the composition, or, optionally, 10 to 30%, 11 to 25%, 12 to 20%, 13 to 15%, 14 to 20%, 15 to 20%, 11 to 15%, or 12 to 14% by weight of the composition.

1.4 Any of the foregoing compositions wherein taurine is present in an amount from about 0.05, 0.1, 0.15, 0.2, 0.3, 0.4, 0.5, 0.6, 0.7, 0.8, 0.9, or 1%, 2%, 3%, 4% up to 5%, or from 0.05, 0.1, 0.15, 0.2, 0.3, 0.4% to 0.5% or 1% by weight of the composition.

1.5 Any of the foregoing compositions wherein aloe extract is present in an amount from about 0.05, 0.1, 0.15, 0.2, 0.3, 0.4, 0.5, 0.6, 0.7, 0.8, 0.9, or 1%, 2%, 3%, 4% up to 5%, or from 0.05, 0.1, 0.15, 0.2, 0.3, 0.4% to 0.5% or 1% by weight of the composition.

1.6 Any of the foregoing compositions in a cosmetically acceptable base suitable for application to the skin, e.g., a cosmetically acceptable base comprising one or more of water-soluble alcohols (such as $C_{2-8}$ alcohols including ethanol); glycols (including propylene glycol, dipropylene glycol, tripropylene glycol and mixtures thereof); glycerides (including mono-, di- and triglycerides); medium to long chain organic acids, alcohols and esters; surfactants (including emulsifying and dispersing agents); additional amino acids; structurants (including thickeners and gelling agents, for example polymers, silicates and silicon dioxide); emollients; fragrances; and colorants (including dyes and pigments).

1.7 The foregoing composition wherein the cosmetically acceptable base is anhydrous, e.g., comprises less than 5% water.

1.8 Any of the foregoing compositions, wherein the composition is an antiperspirant and/or deodorant, e.g., an antiperspirant stick, an aerosol antiperspirant spray, or a liquid roll-on antiperspirant.

1.9 Any of the foregoing compositions, wherein the composition is a body wash, a shower gel, a bar soap, a shampoo, or hair conditioner.

The invention further provides methods of reducing perspiration comprising applying an antiperspirant effective amount of any of Composition 1, et seq. to the skin, methods of reducing body odor comprising applying a deodorant-effective amount of any of Composition 1, et seq. to the skin, and methods of killing bacteria comprising contacting the bacteria with an antibacterially effective amount of a composition, e.g., any of Composition 1, et seq.

The invention further provides a method of making a composition comprising combining the antiperspirant active ingredient, aloe extract and taurine in a cosmetically acceptable base material.

The invention further provides the use of antiperspirant active ingredient, aloe extract and taurine to kill bacteria, reduce perspiration, and/or reduce body odor, wherein the antiperspirant active ingredient contains aluminum, zirconium, zinc or a combination thereof.

Taurine is a colorless crystalline substance, $C_2H_7NO_3S$, an amino sulfonic acid synthesized from L-cysteine. Taurine is also formed by the hydrolysis of taurocholic acid and is found in the fluids of the muscles and other tissues of many animals. Taurine is commercially available as synthetic, or extracts from natural products, from various suppliers, including Sigma-Aldrich Corp., St. Louis, Mo.

Aloe extract is a natural product extracted from the leaves and other parts of the aloe vera plant, *Aloe barbadensis* Mill., or similar varieties of the aloe, which is a widely known clump-forming succulent evergreen plant. Aloe extract, also known as aloe *barbadensis* leaf juice, is commercially available as a powder from various suppliers, including as aloe vera freeze-dried powder 200:1, available from Mexialoe Laborotorios, S.A. de C.V., Campeche, Mexico.

As used herein, the term antiperspirant can refer to any material that can form a plug in a pore to reduce sweating, or antiperspirant refers to those materials classified as antiperspirants by the Food and Drug Administration under 21 CFR part 350. Antiperspirants may also be deodorants, particularly in the case of this invention, as the aluminum, zirconium and zinc-containing active ingredients have antibacterial properties and can reduce odor-causing bacteria on the skin.

Without intending to be bound by theory, it is believed that the combination of aloe and taurine synergistically interact to reduce the irritant potential of antiperspirant active ingredients.

The antiperspirant active ingredients for use in the antiperspirant embodiments of the present invention include any compound, composition or other material having antiperspirant activity. For example, any antiperspirant active ingredients listed in the Food and Drug Administration's Final Monograph on Antiperspirant Drug Products for Over-the-Counter Human Use can be used, especially in the United States. In addition, any new or future ingredient, not listed in the Monograph, can be incorporated as an antiperspirant active for the purpose of this invention. Preferred antiperspirant actives include astringent metallic salts, especially inorganic and organic salts of aluminum, zirconium and zinc, as well as mixtures thereof. Particularly preferred are aluminum-containing and/or zirconium-containing salts or materials, such as aluminum halides, aluminum hydroxyhalides, zirconyl oxyhalides, zirconyl hydroxyhalides, and mixtures thereof. Especially useful antiperspirant actives suitable for use in the formulations include aluminum bromohydrate, aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium chlorohydrate, aluminum zirconium trichlorohydrate, aluminum zirconium tetrachlorohydrate, aluminum zirconium pentachlorohydrate, aluminum zirconium octachlorohydrate, aluminum zirconium tetrachlorohydrex propylene glycol complex, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate, buffered aluminum sulfate, potassium alum, sodium aluminum chlorohydroxy lactate and combinations thereof.

The composition can be any type of personal care composition. In certain embodiments, the composition is any composition in which it is desired to include an antibacterial agent for application to the skin. Examples of such compositions include, but are not limited to, personal care compositions, including, for example, antiperspirants, deodorants, body washes, shower gels, bar soaps, shampoo, hair conditioners, exfoliators, facial cleansers, facial creams, lotions, pharmaceutical compositions, including, for example, acne and other dermatological formulations, oral care compositions, and cosmetic compositions.

The carrier represents all other materials in the composition other than the active ingredient, aloe and taurine. The amount of carrier is then the amount to reach 100% by adding to the weight of the active ingredient, aloe and taurine.

For antiperspirant/deodorant compositions, the carrier can be any carrier that is used for antiperspirants/deodorants. The carrier can be in the form of a stick, a gel, a roll-on, or an aerosol. For stick formulations, the carrier may include oils and/or silicones and gelling agents. An example of a formulation can be found in US2011/0076309A1, incorporated by reference herein.

Optional ingredients that can be included in an antiperspirant and/or deodorant formulation of the compositions of the invention include solvents; water-soluble alcohols such as $C_{2-8}$ alcohols including ethanol; glycols including propylene glycol, dipropylene glycol, tripropylene glycol and mixtures thereof; glycerides including mono-, di- and triglycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments. If desired, an antiperspirant and/or deodorant agent additional to the antiperspirant active ingredient can be included, for example an odor reducing agent such as a sulfur precipitating agent, e.g., copper gluconate, zinc gluconate, zinc citrate, etc.

The antiperspirant compositions can be formulated into topical antiperspirant and/or deodorant formulations suitable for application to skin, illustratively a stick, a gel, a cream, a roll-on, a soft solid, a powder, a liquid, an emulsion, a suspension, a dispersion, an aerosol, or a spray. The composition can comprise a single phase or can be a multi-phase system, for example a system comprising a polar phase and an oil phase, optionally in the form of a stable emulsion. The composition can be liquid, semi-solid or solid. The antiperspirant and/or deodorant formulation can be provided in any suitable container such as an aerosol can, tube or container with a porous cap, roll-on container, bottle, container with an open end, etc.

The compositions can be used in a method to reduce sweating by applying the composition to skin. In certain embodiments, the application is to axilla. Also, the compositions can be used to kill bacteria by contacting bacteria with the composition. For example, in one embodiment, the combination of the active ingredient, aloe and taurine, which can then kill bacteria and reduce sweat.

Thus the invention provides (i) a method for controlling perspiration comprising applying to skin an antiperspirant effective amount of a formulation of any embodiment embraced or specifically described herein, e.g., any of Compositions 1 et seq.; and (ii) a method for controlling odor from perspiration comprises applying to skin a deodorant effective amount of a formulation of any embodiment embraced or specifically described herein, e.g., any of Compositions 1 et seq.

Unless stated otherwise, all percentages of composition components given in this specification are by weight based on a total composition or formulation weight of 100%.

Unless otherwise specifically identified, the ingredients for use in the compositions and formulations of the present invention are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this invention, and includes for example excipients which are "Generally Recognized as Safe" (GRAS) by the United States Food and Drug Administration.

The composition can optionally contain emollients in any desired amount to achieve a desired emollient effect. Emollients are known in the art and are used to impart a soothing effect on the skin. Non-volatile emollients are preferable. Classes of non-volatile emollients include non-silicone and silicone emollients. Non-volatile, non-silicone emollients include $C_{12-15}$ alkyl benzoate. The non-volatile silicone material can be a polyethersiloxane, polyalkyarylsiloxane or polyethersiloxane copolymer. An illustrative non-volatile silicone material is phenyl trimethicone. Non-limiting examples of emollients can be found in U.S. Pat. No. 6,007,799. Examples include, but are not limited to, PPG-14 butyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl)adipate), Di-(2-ethyl hexyl)succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide.

The composition can contain a fragrance. Any known fragrance can be used in any desired amount. In one embodiment, the amount of fragrance is 0.01 to 10 weight %.

Antioxidants may be added to the composition, preferably to act as ingredient protectants and for maintenance of long-term stability of the composition. Examples of antioxidants include, but are not limited to butylated hydroxytoluene, pentaerythrityl tetra-di-t-butyl hydroxyhydrocinnamate.

Any of the liquid antiperspirant/deodorant compositions can be applied to axillary areas to reduce sweat and/or odor. The compositions can be applied by hand or via their packaging.

The present invention moreover relates to a method for prophylaxis of skin irritation, a method for treatment of skin irritation, a method for reducing, eliminating or suppressing the irritating, preferably the skin-irritating, action of a substance or substance mixture, and a kit comprising (i) a formulation, a cosmetic product or a pharmaceutical product according to the present invention and, spatially separated, (ii) one or more substances or substance mixtures having an irritating, preferably a skin-irritating, action.

The problem of sensitive skin affects a growing number of adults and children. It is now assumed that up to 50% of the population have a sensitive skin (L. Misery et al., Ann. Dermatol. Venereol. 2005, 132, 425-429). Sensitive skin describes a skin having a reduced irritation threshold for irritants, such as hyper-reactive, intolerant and also atopic skin. In the case of humans with sensitive, delicate or easily injured skin, a phenomenon called "stinging" can be observed. Typical adverse phenomena associated with the terms "stinging" or "sensitive skin" are reddening of the skin, tingling, prickling, tautness and burning of the skin and itching. They can be caused by stimulating environmental conditions, such as e.g. massage, action of surfactants, influence of weather, such as heat, cold, dryness and also damp heat, thermal radiation and UV radiation, e.g. from the sun, or psychological stress.

In this text, the term "skin" also includes the "mucous membrane" (mucosa), especially the mucous membrane of mouth, throat, gums, nose, respiratory and gastrointestinal tract ("GI tract"). In the cosmetics and pharmaceuticals industry, there is a constant need for agents having an irritation-reducing action.

The mucous membranes, which line various body cavities that are exposed to the external environment and internal organs (e.g. mouth and throat), and the skin in general (in particular the epidermis) are—as barrier organs of the human organism—subjected to external influences to a particular extent. Many intrinsic (e.g. genetic predisposition) and extrinsic (e.g. damage to the skin barrier, action of UV light, irritating or allergy-inducing substances) factors can lead to skin irritation. In connection with this application, "skin irritation" is to be understood as meaning any change to the skin which induces sensorial malaise in humans or animals and/or is characterized by dry, reddened and/or inflamed skin symptoms. The term "sensorial malaise" here of course also includes states such as itching or pain. Skin irritation can include, in particular, several different skin states such as: delicate skin, sensitive skin, including sensitive scalp, easily injured skin, atopic skin (atopy), irritated skin or inflamed skin, which may manifest itself in a reddening of the skin, the so-called erythema. Skin irritations can further include irritations of the oral cavity, like periodontitis, gingivitis and the like, as described in more detail below, irritations like rhinosinusitis (common cold), sinusitis, pharyngitis/tonsillitis and the like, as described in more detail below and in US 2009/0238905, incorporated herein by reference, and irritations of the gastrointestinal tract, as described in more detail below and in US 2009/0238905, incorporated herein by reference.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Two in vitro reconstructed human epidermis models were employed to assess the relative irritation potential of selected test samples, the Cytotoxicity Assay (MTT) and the Irritation Assay (IL-1α Release Assay), described below.

Test Procedures
Cytotoxicity Assay (MTT):

Cell damage was evaluated by assessing mitochondrial metabolic activity using 3-[4,5-dimethylthiazol-2-yl]-2,5-diphenyltetrazolium bromide (MTT-reduction assay) upon exposure to the test sample. MTT solution was prepared as 1.0 mg/ml in Phosphate Buffered Saline (PBS) just before usage. In vitro skin samples (MatTek EpiDerm) were treated topically with the test sample for 1 hour in a tissue culture incubator. Following the incubation, skin samples were washed with PBS and placed in 24 well tissue culture plates, and 500 µl of the MTT solutions were added to each well and incubated at 37° C. for 2 hours. The cell survivability was analyzed by measuring the ability of the cell's mitochondria to reduce the colorless MTT to a colored formazan crystalline end product. The reaction was terminated by the removal of the MTT solution from the wells. Addition of 1.0 mL of 0.04M HCl in isopropanol to each well was used to dissolve the intracellular MTT formazan crystals. The contents of each well were mixed gently in an orbital shaker at room temperature for 1 hour and the absorbency at 570 nm was measured by an ELISA plate reader (SpectraMax M5 Multi-Mode Microplate Readers, Molecular Devices, California).

Irritation Assay (IL-1α Release Assay):

To document the skin irritation of Antiperspirant Active Ingredients, we have conducted in vitro experiments using 3D EpiDerm skin models (SIT-200 skin irritation model, MatTek Corporation, Ashland, Mass. 01721). In vitro skin samples were treated topically with the test compound for 1 hour in tissue culture incubator. Following the incubation, skin samples were washed with PBS and placed in a culture medium and continue to incubate for 24 hours. Cell culture media was collected for IL-1α release assay. Higher the IL-1a release means higher the irritation potential. IL-1α release was analyzed by ELISA assay kit (Invitrogen, Grand Island, N.Y. 14072) and (R&D Systems, Minneapolis, Minn. 55413).

Formulations

The surprising synergistic effectiveness of aloe vera and taurine together is demonstrated in formulations containing various antiperspirant active ingredients at levels that are demonstrated to cause skin irritation, as further described in the formulations and test results set forth below.

Materials

The materials used in the examples are summarized on Table 1, below.

TABLE 1

| Ingredient Name | Description | Source |
| --- | --- | --- |
| Aluminum Chloride Hexaaqua | Reagent Grade Crystalline | Alfa Aesar |
| ACH Solution 50% | Aluminum chloride hexaaqua in water | Prep |
| Aloe Vera Freeze Dried Powder 200:1 | Aloe Barbadensis Leaf Juice | Mexi Aloe Lab |
| Alum | Potassium Aluminum Sulfate Crystals | |
| BHT | Butylated hydroxytoluene | |
| Caprylyl glycol | | Inolex |
| Cetyl alcohol | | BASF |
| Cyclomethicone | | |
| Dimethicone | | |
| Flexithix | | Ashland |
| Fragrance | Lizzy | |
| Glycerin | | P&G |
| Isopropyl myristate | | BASF |
| Natragem EW | Emulsifying wax-Glyceryl Stearate, Polyglyceryl-6 Palmitate/Succinate, Cetearyl Alcohol | Croda |

TABLE 1-continued

| Ingredient Name | Description | Source |
|---|---|---|
| Polawax | Emulsifying wax-general purpose vegetable derived | Croda |
| Phenoxy ethanol | | |
| PPG-15 Stearyl ether | Polypropylene glycol stearyl ether | Croda |
| Steareth-2 | Polyethylene glycol stearyl ether | Croda |
| Steareth-21 | Polyethylene glycol stearyl ether | Croda |
| Talcum powder | Pharma type | |
| Taurine | | Sigma-Aldrich |
| UltraZAG 88 L | Zirconium/Aluminum Salt | SummitReheis |

Example 1

Samples were prepared according to Table 2 by adding the amounts of anti-irritating agents and then diluting to a final solution weight using PBS solution. Then, 500 μl of 28% of aluminum chloride hexaaqua solution and 500 μl of anti-irritating agent solutions are added together for usage when treating tissue cultures.

TABLE 2

| Sample | AlCl$_3$•6H$_2$O (g) | Anti-Irritating Agt. (g) | Total (g) | % |
|---|---|---|---|---|
| Untreated | | | | |
| AlCl$_3$ Control | 1.029 | 0 | 3.647 | 28% |
| Taurine | 0 | 0.08 | 20.00 | 0.4% |
| Aloe | 0 | 0.0498 | 12.45 | 0.4% |

Experimental results are illustrated in Table 3. Taurine and aloe each individually reduced the irritant and cytotoxic effect of the antiperspirant active, however the combination of taurine and aloe had an unexpectedly greater effect. These results suggest a synergistic anti-irritant action of taurine when combined with aloe extract. The MTT assay for cytotoxicity test reveals that AlCl$_3$.6H$_2$O AP salt solution cause decreases in cell viability, as further illustrated in the graph of FIG. 1. Irritation assay measures IL-1α release to evaluate the level of skin irritation, the greater IL-1α released, the greater the irritation potential.

TABLE 3

| Sample | MTT | IL-1α |
|---|---|---|
| Control | 100 | 100 |
| 14% AlCl$_3$ | 78 | 345 |
| 14% AlCl$_3$ + 0.2% Aloe | 75 | 175 |
| 14% AlCl$_3$ + 0.2% Taurine | 68 | 170 |
| 14% AlCl$_3$ + 0.1% Taurine + 0.1% Aloe | 83 | 99 |

The data on Table 3 show that the tissue treated with AlCl$_3$.6H$_2$O AP salt solution releases significantly higher percentages of IL-1α as compared to the untreated tissue. It can be concluded that high irritation potential is found in AlCl$_3$.6H$_2$O AP salt treated tissue. This cytotoxicity and irritation/inflammation effects of AlCl$_3$.6H$_2$O AP salt is significantly reduced by the synergistic combination of aloe extract with taurine, which data is also presented on the graph of FIG. 2.

Example 2

Samples were prepared according to Table 4 by adding the indicated amounts of anti-irritating agents and then diluting to a final solution weight using PBS solution. Then, 500 μl of 28% of aluminum chloride hexaaqua solution and 500 μl of anti-irritating agent solutions are added together for usage when treating tissue cultures.

TABLE 4

| Sample | AlCl$_3$•6H$_2$O (g) | Anti-Irritating Agt. (g) | Total (g) | % |
|---|---|---|---|---|
| Untreated | | | | |
| AlCl$_3$ Control | 1.27 | 0 | 4.54 | 28% |
| Taurine | 0 | 0.026 | 13.23 | 0.20% |
| Aloe | 0 | 0.0204 | 9.57 | 0.20% |
| Taurine | 0 | 0.104 | 10.47 | 1.00% |
| Aloe | 0 | 0.144 | 14.23 | 1.00% |

A study was conducted that revealed the synergistic effects that taurine exhibit when combined with aloe to reduce irritation when tissue cultures were irritated with AlCl$_3$. MTT assay for cytotoxicity test reveals that AlCl$_3$.6H$_2$O AP salt solution has reduced 15-20% cell viability compared to untreated tissue (shown in Table 5), which suggests cytotoxicity effects of AlCl$_3$.6H$_2$O AP salt solution.

TABLE 5

| Sample | MTT | IL-1α |
|---|---|---|
| Control | 100 | 100 |
| 14% AlCl$_3$ | 84 | 594 |
| 14% AlCl$_3$ + 0.1% Taurine | 79 | 389 |
| 14% AlCl$_3$ + 0.1% Aloe | 78 | 338 |
| 14% AlCl$_3$ + 0.1% Taurine + 0.1% Aloe | 95 | 139 |
| 14% AlCl$_3$ + 0.5% Taurine | 79 | 369 |
| 14% AlCl$_3$ + 0.5% Aloe | 79 | 286 |
| 14% AlCl$_3$ + 0.5% Taurine + 0.5% Aloe | 93 | 226 |

The cytotoxic effects are seen in the AlCl$_3$ control and slight improvements are shown when the tissues are treated with aloe or taurine, separately. However, when the tissues are treated with aloe and taurine together, a synergistic effect can be seen and an unexpected degree of increase in cell viability occurs, as illustrated in the graph of FIG. 2. Irritation assay measures IL-1α release to evaluate the level of skin irritation, the greater IL-1α released, the greater the irritation potential. Table 5 shows that the tissue treated with AlCl$_3$.6H$_2$O AP salt solution releases significantly higher percentages of IL-1α as compared to the untreated tissue. Thus, high irritation potential is found in AlCl$_3$.6H$_2$O AP salt treated tissue. The cytotoxicity and irritation/inflammation effects of AlCl$_3$.6H$_2$O AP salt are significantly reduced by the synergistic combination of aloe extract with taurine (shown in Table 5).

MTT and IL-1α assays demonstrate the unique synergistic anti-irritant effect of aloe and taurine across a wide range, between 0.1%-1%. IL-1α levels are significantly lower in the tissue cultures that are treated with aloe and taurine individually, however an additional synergistic effect can be seen when both aloe and taurine are used together.

Example 3. Formulated Samples

Prototype products were made according to the following procedure. Demineralized water, caprylyl glycol, and aluminum chloride were added together to the main beaker. Glycerin, isopropyl myristate and flexithix were pre-mixed in a separate beaker and then added into the main beaker, which was then placed under Greerco Homogenizer and homogenized at 50 rpm for 15-20 minutes. The pH, viscosity and temperature of the completed batch were measured. A base product with a 1% hole (Table 6) was made so that the indicated amount of taurine and aloe extract could be added at a later time along with an amount of water such that the water and the stated amount of taurine and aloe, if any, make up the 1 weight percent in total.

TABLE 6

Prototype Composition

| Ingredient | % |
| --- | --- |
| $H_2O$ | 72.6 |
| Flexithix | 4 |
| Glycerin | 5 |
| IPM | 5 |
| Cap glyc | 0.3 |
| $AlCl_3$ | 12.1 |
| Hole | 1 |
| Total | 100 |

Another formulation was made and tested for irritation. This $AlCl_3$ cream formulation was made according to the table below (Table 7). The base product with a 1% hole was made so that taurine and aloe extract could be added at a later time at the 0.1% concentrations that are being tested in these studies, and the balance of the 1% hole is made up with water.

TABLE 7

$AlCl_3$ Cream Composition

| Ingredient | % |
| --- | --- |
| $H_2O$ | 64.6 |
| Natragem | 6 |
| Glycerin | 10 |
| Steareth-21 | 1 |
| Cap glyc | 0.3 |
| $AlCl_3$ | 12.1 |
| Hole | 1 |
| Isopropyl myristate | 2.5 |
| Cetyl Alcohol | 2.5 |
| Total | 100 |

Two studies were conducted that revealed the anti-irritating effects of taurine and aloe extract when tissue cultures were irritated with prototype antiperspirant product or $AlCl_3$ cream product that contained 12% $AlCl_3$. The tissue cultures were treated with high enough amounts of the samples to induce irritation (IL-1α expression), but not cytotoxic effects since products that result in large reductions in cell viability would be harmful to the skin, the results are reported on Table 8, below.

TABLE 8

| Sample | MTT | IL-1α |
| --- | --- | --- |
| Control | 100 | 100 |
| 12% $AlCl_3$ | 99 | 234 |
| 12% $AlCl_3$ Prototype | 83 | 258 |
| 12% $AlCl_3$ Prototype + 0.1% Taurine + 0.1% Aloe | 94 | 187 |

The MTT assay for cytotoxicity test (Table 8) reveals slight decreases in cell viability in some of the tissue treated with products that contain $AlCl_3$. This suggests that the products would not cause significant cell death in human skin and demonstrates skin mildness.

Irritation assay measures IL-1α release to evaluate the level of skin irritation, the greater IL-1α released, the greater the irritation potential. Table 8 shows that the tissue treated with $AlCl_3.6H_2O$ AP salt solution, and 12% $AlCl_3$ formulated product with no anti-irritant additives, release significantly higher percentages of IL-1α as compared to the untreated tissue. Table 8 also shows similar results where tissue treated with a 12% AlCl cream with no additives release significantly higher percentages of IL-1α as compared to the untreated tissue. It can be concluded that high irritation potential is found in $AlCl_3.6H_2O$ AP salt treated tissue, 12% $AlCl_3$ formulated product treated tissue and 12% $AlCl_3$ cream product treated tissue. These cytotoxic and irritation/inflammation effects of $AlCl_3.6H_2O$ AP salt are significantly reduced by the combination of aloe extract with taurine (Table 8).

Example 4

Product Preparation:

The 12% ACH and 12% ZAG Cream products were made based on the formulations presented in Table 9 and 10. A 1% hole is left in the base cream formulation to add taurine and aloe extract at a later time. Taurine and aloe concentrations were either added at 0.1% or 0.05% concentrations into the formulation.

TABLE 9

12% ACH Cream Composition

| Ingredient | % |
| --- | --- |
| $H_2O$ | 44.1 |
| Cetyl Alcohol | 2.5 |
| Glycerin | 10 |
| Isopropyl myristate | 2 |
| Cap glyc | 0.3 |
| ACH Solution | 30 |
| Ceral PW | 9 |
| Fragrance: Lizzy | 1.1 |
| Hole | 1 |
| Total | 100 |

TABLE 10

12% ZAG Cream Composition

| Ingredient | % |
| --- | --- |
| $H_2O$ | 34.6 |
| UltraZAG 88 L | 37.5 |
| Glycerin | 10 |
| Steareth-21 | 1 |
| Cap glyc | 0.3 |
| Polawax | 9 |

TABLE 10-continued

12% ZAG Cream Composition

| Ingredient | % |
|---|---|
| Hole | 1 |
| Isopropyl myristate | 2 |
| Cetyl alcohol | 2.5 |
| Fragrance: Lizzy | 1.1 |
| Total | 100 |

A study was conducted that revealed the anti-irritating effects of taurine and aloe extract when tissue cultures were irritated with 12% ACH and 12% ZAG cream antiperspirant products. The tissue cultures were treated with amounts of the samples to induce irritation (IL-1α expression). The results are reported on Table 11

TABLE 11

| Sample | MTT | IL-1α |
|---|---|---|
| Control | 100 | 100 |
| 12% ACH Cream | 92 | 180 |
| 12% ACH Cream + 0.1% Taurine + 0.1% Aloe | 93 | 118 |
| 12% ZAG Cream | 91 | 139 |
| 12% ZAG Cream + 0.1% Taurine + 0.1% Aloe | 86 | 111 |
| 12% ZAG Cream + 0.05% Taurine + 0.05% Aloe | 83 | 113 |

Irritation assay measures IL-1α release to evaluate the level of skin irritation, the greater IL-1α released, the greater the irritation potential. Table 11 shows that the tissue samples treated with 12% ACH and ZAG cream product without the studied additives release significantly higher percentages of IL-1α as compared to the untreated tissue. It can be concluded that higher irritation potential is found in the ACH and ZAG cream product treated tissue. These cytotoxic and irritation/inflammation effects of ACH and ZAG are significantly reduced by the combination of aloe extract with taurine (shown in Table 11). The 12% ACH cream product with 0.1% aloe and 0.1% taurine show significantly lower IL-1α release compared to 12% ACH cream product with no anti-irritant additives. Similar results are seen for 12% ZAG cream product with 0.1% and 0.05% concentrations of aloe and taurine.

MTT and IL-1α assays (Table 11) complementarily demonstrate the anti-irritant effect of aloe extract and taurine in ACH and ZAG cream antiperspirant product formulations. IL-1α levels are significantly lower in the tissue cultures that are treated with the products that contain aloe and taurine at 0.1% and 0.05% concentrations compared to the products that do not contain these ingredients. This study has shown that the synergistic anti-irritant combination of taurine and aloe extract can be extended into formulations to reduce skin irritation caused by ACH and ZAG.

Example 5

Sample Preparation:

The 12% ACH and 2% Alum roll-on antiperspirant products were made based on the formulations presented in Table 12 and 13. After the base products were made according to the tables below, taurine and aloe concentrations were either added at 0.1% or 0.05% concentrations into the base formulation to create the final formulation.

TABLE 13

2% Alum Roll-On Composition

| Ingredient | % |
|---|---|
| H20 | 80.994 |
| Potassium Aluminum Sulfate Crystals | 2.106 |
| Glycerin | 4.210 |
| Steareth-21 | 1.580 |
| Cap glyc | 0.530 |
| Phenoxy Ethanol | 0.630 |
| PPG-15 Stearyl Ether | 3.680 |
| Cyclomethicone | 2.110 |
| Dimethicone 20/CS | 0.530 |
| Steareth-2 | 3.370 |
| BHT | 0.05 |
| Talcum powder | 0.210 |
| Total | 100 |

TABLE 12

12% ACH Roll-On Composition

| Ingredient | % |
|---|---|
| H20 | 59.10 |
| PPG-15 Stearyl Ether | 3.680 |
| Glycerin | 4.21 |
| Cyclomethicone | 2.11 |
| Cap glyc | 0.32 |
| 50% ACH Solution | 24.840 |
| Dimethicone 20/CS | 0.530 |
| Steareth-21 | 1.580 |
| Steareth-2 | 3.370 |
| BHT | 0.050 |
| Talcum powder | 0.210 |
| Total | 100 |

A study was conducted that revealed the anti-irritating effects of taurine and aloe extract when tissue cultures were irritated with 12% ACH and 2% Alum antiperspirant products, reported on Table 14, below.

TABLE 14

| Sample | MTT | IL-1α |
|---|---|---|
| Control | 100 | 100 |
| 2% Alum | 98 | 178 |
| 2% Alum + 0.1% Aloe + 0.1% Taurine | 89 | 125 |
| 2% Alum + 0.05% Aloe + 0.05% Taurine | 83 | 97 |
| High ACH Roll-On | 94 | 190 |
| High ACH + 0.05% Aloe + 0.05% Taurine | 90 | 128 |
| High ACH + 0.1% Aloe + 0.1% Taurine | 100 | 105 |

The tissue cultures were treated with amounts of the samples to induce irritation (IL-1α expression). The MTT assay for cytotoxicity test (Table 14) reveals only slight decreases in cell viability in some of the tissue treated with products that contain ACH or Alum.

Irritation assay measures IL-1α release to evaluate the level of skin irritation, the greater IL-1α released, the greater the irritation potential. Table 14 shows that the tissue treated with 12% ACH and 2% Alum products with no anti-irritant additives release significantly higher percentages of IL-1α as compared to the untreated tissue. It can be concluded that higher irritation potential is found in 12% ACH and 2% Alum product treated tissues. This cytotoxic and irritation/inflammation effects of ACH and Alum is significantly reduced by the combination of aloe extract with taurine (shown in Table 14). The 12% ACH product with 0.1% aloe and 0.1% taurine and 0.05% aloe and 0.05% taurine show significantly lower IL-1α release compared to 12% ACH cream product with no additives. Similar results are seen for 2% Alum product with 0.1% and 0.05% concentrations of aloe and taurine. Experimental results are illustrated in Table 14. These results demonstrate that the anti-irritating effects of taurine and aloe extract are applicable to ACH and Alum roll-on antiperspirant products.

MTT and IL-1α assays complementarily demonstrate the anti-irritant effect of aloe extract and taurine in ACH and Alum roll-on antiperspirant product formulations. IL-1α levels are significantly lower in the tissue cultures that are treated with the products that contain aloe and taurine at 0.1% and 0.05% concentrations compared to the products that do not contain any of these ingredients.

What is claimed is:

1. A personal care composition comprising about 2 to 40 weight percent of an active ingredient, wherein the active ingredient is a metal-containing antiperspirant active ingredient, in combination with aloe extract and taurine, wherein a total amount of aloe extract is 0.01 to 5 weight percent, and a total amount of taurine is 0.01 to 5 weight percent, in an acceptable carrier, all based on the total weight of the composition, wherein the aloe extract and taurine are present in a synergistic combination to reduce cytotoxicity and irritation/inflammation effects of the metal-containing antiperspirant active ingredient.

2. The personal care composition according to claim 1, wherein the metal-containing antiperspirant active ingredient contains aluminum, zirconium, zinc or a combination thereof.

3. The personal care composition according to claim 1, wherein the metal-containing antiperspirant active ingredient is selected from aluminum-containing and/or zirconium-containing salts or metal complexes.

4. The personal care composition according to claim 1, wherein the metal-containing antiperspirant active ingredient is selected from aluminum halides, aluminum hydroxyhalides, zirconyl oxyhalides, zirconyl hydroxyhalides and combinations thereof.

5. The personal care composition according to claim 1, wherein the metal-containing antiperspirant active ingredient is selected from aluminum bromohydrate, aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium chlorohydrate, aluminum zirconium trichlorohydrate, aluminum zirconium tetrachlorohydrate, aluminum zirconium pentachlorohydrate, aluminum zirconium octachlorohydrate, aluminum zirconium tetrachlorohydrex propylene glycol complex, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate, buffered aluminum sulfate, potassium alum, sodium aluminum chlorohydroxy lactate and combinations thereof.

6. The personal care composition according to claim 1, wherein a total amount of the metal-containing antiperspirant active ingredient present in the composition is 5 to 40 wt. %, based on the total weight of the composition.

7. The personal care composition according to claim 1, wherein a total amount of the metal-containing antiperspirant active ingredient present in the composition is 10 to 30% by weight, based on the total weight of the composition.

8. The personal care composition according to claim 1, wherein a total amount of taurine is 0.05 to 5 wt. %, based on the total weight of the composition.

9. The personal care composition according to claim 1, wherein a total amount of aloe extract is 0.05 to 5 wt. %, based on the total weight of the composition.

10. The personal care composition according to claim 1, wherein a total amount of aloe extract is 0.05% to about 1% by weight of the composition, and a total amount of taurine is 0.05% to about 1 wt. %, based on the total weight of the composition.

11. The personal care composition according to claim 1, wherein a total amount of aloe extract is 0.05 to about 0.5 wt. %, and a total amount of taurine is 0.05 to about 0.5 wt. %, based on the total weight of the composition.

12. The personal care composition according to claim 1, wherein the acceptable carrier comprises one or more ingredients selected from water-soluble alcohols; glycols; glycerides; medium to long chain organic acids, alcohols and esters; surfactants; additional amino acids; structurants; emollients; fragrances; and colorants.

13. The personal care composition according to claim 1, wherein the composition is an antiperspirant and/or a deodorant.

14. The personal care composition according to claim 1, wherein the acceptable carrier is anhydrous.

15. The personal care composition according to claim 1, wherein the composition is a body wash, a shower gel, a bar soap, a facial cleanser, a lotion, a shampoo, or hair conditioner.

16. A method of reducing sweat and/or body odor comprising applying the composition of claim 1 to skin.

17. A method of killing bacteria comprising contacting the bacteria with a composition of claim 1.

* * * * *